(12) United States Patent
Muraca

(10) Patent No.: US 6,716,619 B1
(45) Date of Patent: Apr. 6, 2004

(54) STYLET FOR USE WITH TISSUE MICROARRAYER AND MOLDS

(75) Inventor: Patrick J. Muraca, Pittsfield, MA (US)

(73) Assignee: Clinomics Biosciences, Inc., Pittsfield, MA (US)

(*) Notice: Subject to any disclaimer, the term of this patent is extended or adjusted under 35 U.S.C. 154(b) by 264 days.

(21) Appl. No.: 09/779,187

(22) Filed: Feb. 8, 2001

(51) Int. Cl.[7] ............................................. C12M 1/00
(52) U.S. Cl. ........................ 435/283.1; 435/309.1; 73/864.44; 600/567
(58) Field of Search .................. 435/283.1, 309.1, 435/286.2, 286.3; 83/684, 919; 30/316; 600/567; 73/864.44

(56) References Cited

U.S. PATENT DOCUMENTS

| | | | | | |
|---|---|---|---|---|---|
| 2,615,245 | A | * | 10/1952 | Schaumleffel | 30/130 |
| 2,623,521 | A | * | 12/1952 | Shaw | 604/170.02 |
| 3,630,192 | A | * | 12/1971 | Jamshidi | 600/567 |
| 3,689,595 | A | * | 9/1972 | Gwinn | 525/89 |
| 4,007,653 | A | * | 2/1977 | Cady | 83/140 |
| 5,040,542 | A | * | 8/1991 | Gray | 600/567 |
| 5,190,169 | A | * | 3/1993 | Sincock | 211/60.1 |
| 5,392,790 | A | * | 2/1995 | Kanner et al. | 600/566 |
| 5,515,861 | A | * | 5/1996 | Smith | 600/567 |
| 5,804,384 | A | | 9/1998 | Muller et al. | 435/6 |
| 6,036,698 | A | * | 3/2000 | Fawzi et al. | 606/114 |
| 6,103,479 | A | | 8/2000 | Taylor | 435/7.2 |
| 6,103,518 | A | | 8/2000 | Leighton | 435/286.3 |
| 6,165,709 | A | | 12/2000 | Friend et al. | 435/4 |

FOREIGN PATENT DOCUMENTS

| | | |
|---|---|---|
| EP | 0 238 190 | 9/1987 |
| EP | 1 026 260 | 8/2000 |
| WO | 99/43855 | 9/1999 |
| WO | 99/44062 | 9/1999 |
| WO | 99/44063 | 9/1999 |
| WO | 00/24940 | 5/2000 |

OTHER PUBLICATIONS

Moch, et al., "Tissue Microarrays: What Will They Bring to Molecular and Anatomic Pathology," Advances in Anatomic Pathology 8(1): Jan. 14–20, 2001.

* cited by examiner

*Primary Examiner*—William H. Beisner
(74) *Attorney, Agent, or Firm*—Palmer & Dodge LLP

(57) ABSTRACT

A stylet for use with an automatic tissue microarrayer is provided for arraying frozen tissue samples on a substrate. In one embodiment, the stylet comprises a stylet needle having a pushing surface for pushing either frozen tissue or embedding media out of a coring needle, and a connecting end. In another embodiment the stylet comprises a stylet body which comprises a stylet base for sliding along the length of the needle and a stylet cap for coupling to the connecting end of the stylet needle. In a further embodiment of the invention, the stylet base and stylet cap are separated from each other by a resilient element, such as a spring. Molds for generating component parts of the stylet are also provided.

21 Claims, 16 Drawing Sheets

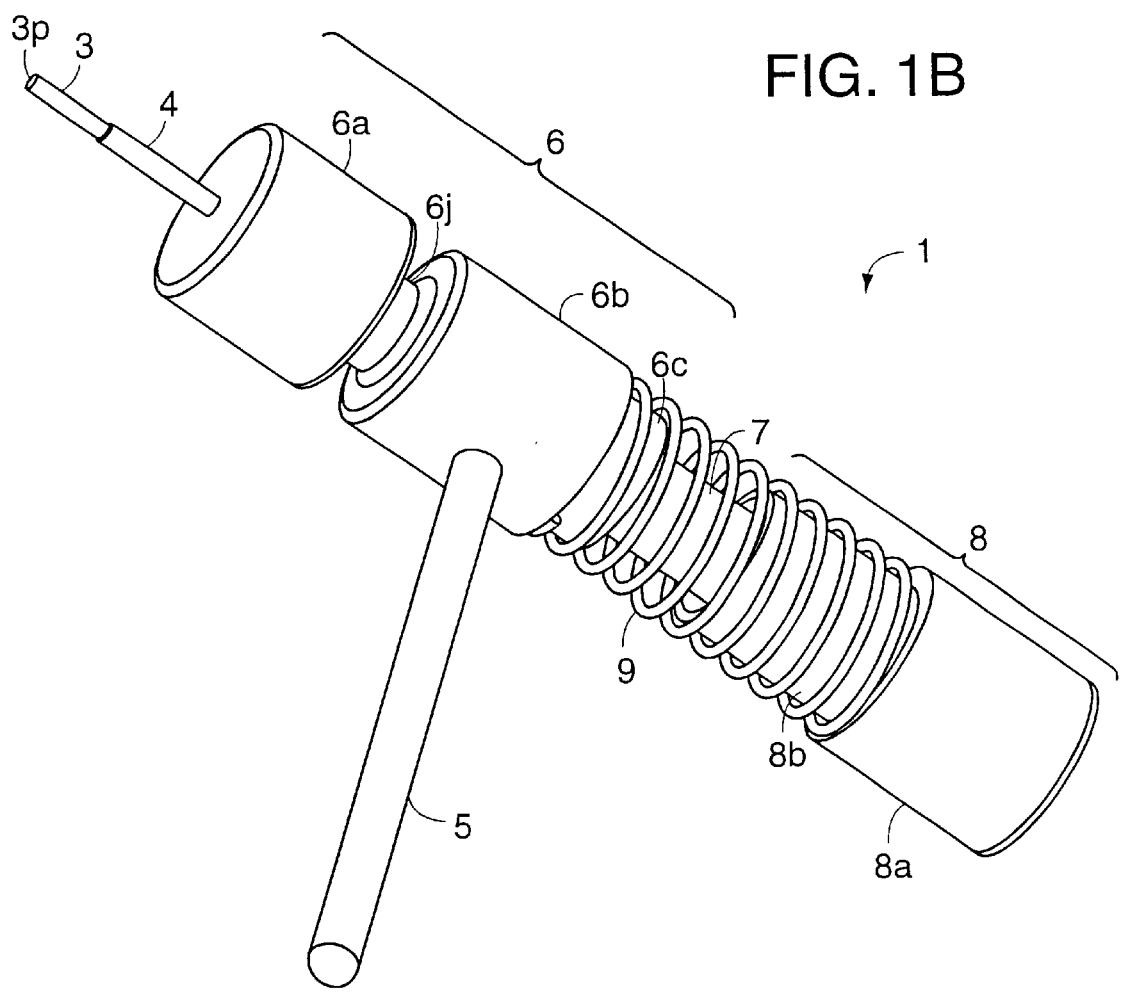

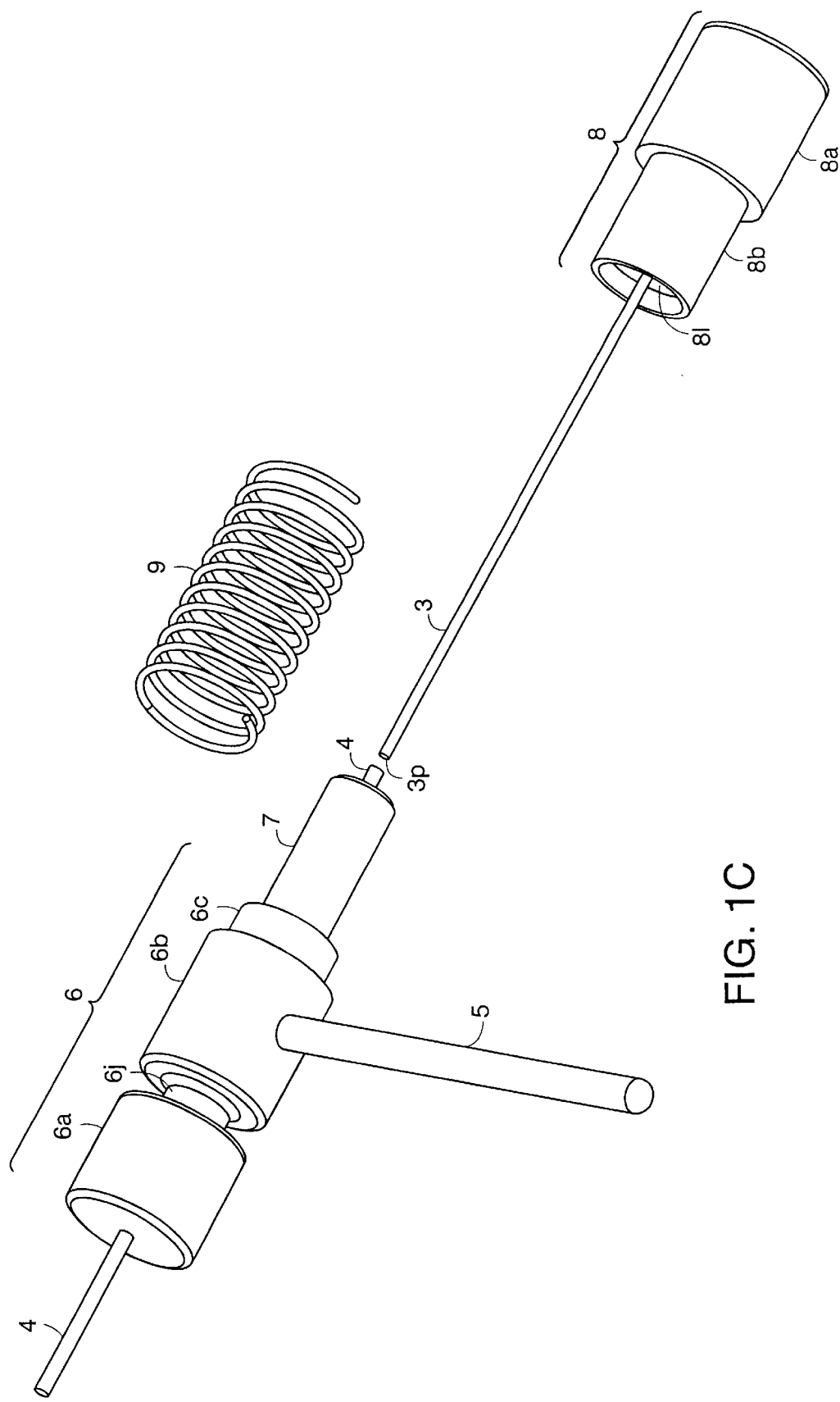

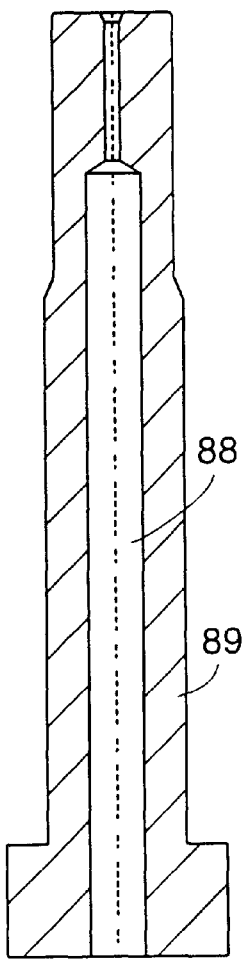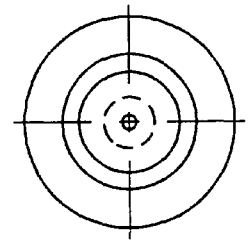
FIG. 6B
FIG. 6A
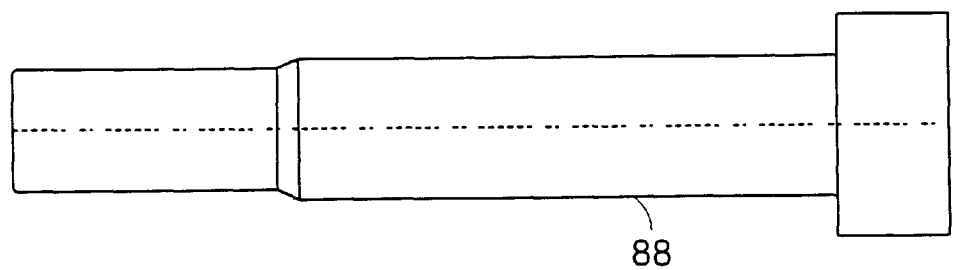
FIG. 6C

STYLET FOR USE WITH TISSUE MICROARRAYER AND MOLDS

FIELD OF THE INVENTION

The invention relates to a sylet for use with an automatic tissue microarrayer. In one embodiment, the invention relates to a stylet which is particularly suited for use in arraying frozen tissues. The invention further relates to molds for generating the stylet.

BACKGROUND

Tissue microarrays increase the throughput of molecular analyses by simultaneously arraying protein, nucleic acids and other biomolecules. Methods of generating tissue microarrays generally include removing tissue slices or cores from paraffin blocks and re-embedding these. For example, Battifora, Laboratory Investigation, 55:244–248, 1986; and U.S. Pat. No. 4,820, 504, teaches forming multiple tissue samples into rods, bundling the rods into a casing, embedding the encased rods in paraffin and sectioning them. Although the method arrays multiple tissue samples, it is difficult to determine the identity of tissues within the array.

In U.S. Pat. No. 5,002,377, Battifora describes cutting tissue samples into strips, positioning the strips into parallel grooves in a mold, and embedding the strips in paraffin. Embedded strips are stacked, forming an embedded block comprising multiple tissue samples. The method is time consuming and is performed manually.

Automatic tissue microarrayers are described in U.S. Pat. No. 6,103,518, the entirety of which is incorporated herein by reference. The arrayer comprises two hollow needle punches; one for punching a hole in a recipient block comprising paraffin and one for removing a core of paraffin embedded tissue from a sample or donor block. A stylet is used to remove the core of tissue from the donor punch and to push the core of tissue into the hole left in the recipient block. The same, or a different stylet, is used to remove embedding matrix from the recipient punch so that it can be reused. The stylet is in communication with a stylet driver which controls the movement of the stylet.

Although the stylet described in U.S. Pat. No. 6,103,518 can be used to array multiple tissue samples, the stylet functions optimally with paraffin-embeddded samples. However, it is desirable for particular molecular analyses to use frozen tissue samples, particularly in analyses which are geared to examining nucleic acid expression in a tissue sample while maintaining good tissue morphology. It is further desirable in view of the need for high throughput arraying, to provide a stylet that is resistant to breakage, can be reused multiple times, and is inexpensive to manufacture.

SUMMARY OF THE INVENTION

The invention provides a stylet for use with an automatic tissue microarrayer which is particularly suitable in the generation of frozen tissue microarrays. The stylet can be used repetitively, greatly increasing the throughput of methods for microarraying frozen tissue. Further, the stylet according to the invention is manufactured from inexpensive plastic materials and is therefore disposable.

In one embodiment, the invention provides a stylet for removing tissue or embedding media from a coring needle and a mold for generating such a stylet. The invention comprises a stylet needle comprising a pushing surface for pushing tissue or embedding media from the coring needle, and a connecting end for connecting the needle to a stylet body. The pushing surface of the stylet needle comprises a material which can maintain a temperature from at least −20° to 4° C. during the process of removing tissue or embedding material from the coring needle. In one embodiment, the stylet needle comprises stainless steel or a plastic that withstands low temperature impact forces. In a preferred embodiment, the stylet needle is at least partially enclosed within a stylet tube.

In one embodiment, the stylet body comprises a lumen for receiving at least the connecting end of the stylet needle and for preventing rotation of the stylet needle within the stylet body. In a preferred embodiment, the stylet body comprises polypropylene or brass. In another embodiment, the stylet body comprises a stylet base for slideably moving along the length of the stylet needle. In a further embodiment, the stylet comprises a cap for coupling to the connecting end of the stylet needle. In still another embodiment of the invention, the stylet base and stylet cap are separated by a resilient element. In a preferred embodiment, the resilient element is a spring.

In one embodiment, the stylet body comprises an opening for receiving a graspable element. In a preferred embodiment, the stylet comprises a graspable element partially inserted within the opening.

In one embodiment, the invention comprises molds for use in generating the stylet. In a preferred embodiment of the invention, a mold comprises two connectable halves, each half comprising a half mold cavity corresponding in shape to half of at least one external component of the shaft (e.g., the needle, the shaft base, the shaft cap, the graspable element). The mold halves are connectable by connecting elements (e.g., connecting pins, screws, or bolts) which align the mold halves and form a whole mold cavity which provides an impression corresponding in shape to a particular component of the shaft. By injecting the appropriate material into the mold through an opening in communication with the whole mold cavity, the components of the shafts are generated.

BRIEF DESCRIPTION OF THE DRAWINGS

The objects and features of the invention can be better understood with reference to the following detailed description and accompanying drawings. Reference numbers in the figures refer to the same details throughout. Although the scale shown in the Figures in 4:1, the relative proportions and sizes of the components of the stylet can vary, and the dimensions indicated reflect only one embodiment of the invention.

FIG. 1B shows a side perspective view of the stylet shown in FIG. 1A.

FIGS. 1C and 1D shows side perspective view of the component parts of the stylet shown in FIGS. 1A–B.

FIG. 2A shows a side view of a stylet needle according to one embodiment of the invention. FIG. 2B shows a side view of a stylet tube for enclosing at least a portion of the stylet needle. FIG. 2C shows a cross-section through the longitudinal axis of the stylet illustrating how the stylet needle and stylet tube fit within the stylet body.

FIG. 4A shows a transverse cross-section through a portion of the stylet cap indicated by an arrow in FIG. 4B. FIG. 4B shows a longitudinal cross-section through longitudinal axis of the stylet cap.

FIGS. 6A–C, show different views of a mold for forming the stylet cap 8 according to one embodiment of the invention and suitable dimensions of the mold.

DETAILED DESCRIPTION

With reference to FIG. 1, the stylet according to the invention is tailored for use in generating frozen tissue microarrays. In one embodiment of the invention, the stylet is used with an automatic, semi-automatic, or manual tissue microarrayer. Types of tissue microarrayers suitable for use with the stylets according to the invention are disclosed in U.S. Provisional Application Serial No. 60/213,321, filed Jun. 22, 2000, U.S. Provisional Application, Serial No. 60/234,493, filed Sep. 22, 2000, U.S. Provisional Application Serial No. 60/236,649, filed Sep. 29, 2000, and U.S. patent application Ser. No. 09/779,753, filed Feb. 8, 2001, entitled, "Frozen Tissue Microarrayer," the entireties of which are incorporated herein by reference.

In one embodiment according to the invention, the stylet is used with an automatic tissue microarrayer which comprises at least one coring needle comprising a cutting edge and a lumen. The cutting edge of the coring needle provides an edge for cutting a frozen tissue block (e.g., frozen tissue embedded in OCT™, Histoprep®, TBS, CRYO-Gel®, Cryomatrix™, and gelatin) while the lumen receives a tissue sample cut out of the frozen tissue block. In one embodiment, the coring needle comprises stainless steel which is precooled to −20° to 4° C. prior to contacting the intended tissue sample. In another embodiment of the invention, the automatic tissue microarrayer comprises at least two coring needles, one for removing a core of embedding matrix from a recipient block, and another for removing a tissue sample from a donor block.

The coring needles may be positioned manually or automatically using an actuator in communication with the needles. In order to facilitate the coring and tissue placement process, the stylets according to the invention are designed to optimally remove embedding media for embedding frozen tissue from a coring needle, preventing the needle from becoming clogged with the embedding media and without melting the embedding media upon contact. Similarly either the same or a different stylet is used to cut frozen tissue from a sample or donor block, preventing the needle from becoming clogged with tissue residue. In a preferred embodiment of the invention, the stylet can be used at least one hundred times to remove tissue and/or embedding material from a coring needle. Still more preferably, the stylet can be reused at least 500 times, or at least 1000 times.

Figure 1A:
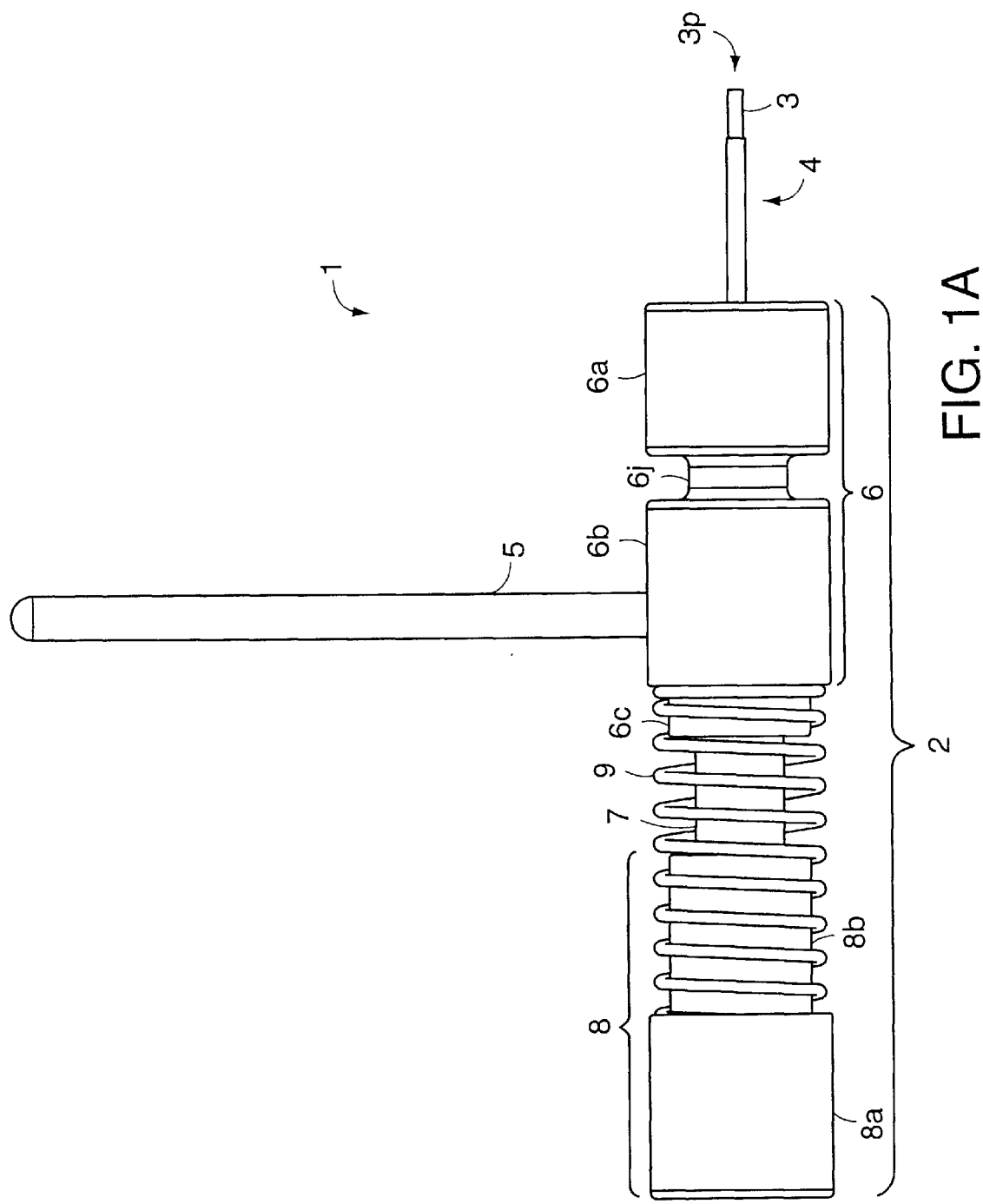
FIG. 1A shows a side view of a stylet according to one embodiment of the invention comprising a stylet needle and stylet body and a handle for facilitating movement of the stylet. The body comprises two sections separated by a spring.
Figure 1D:
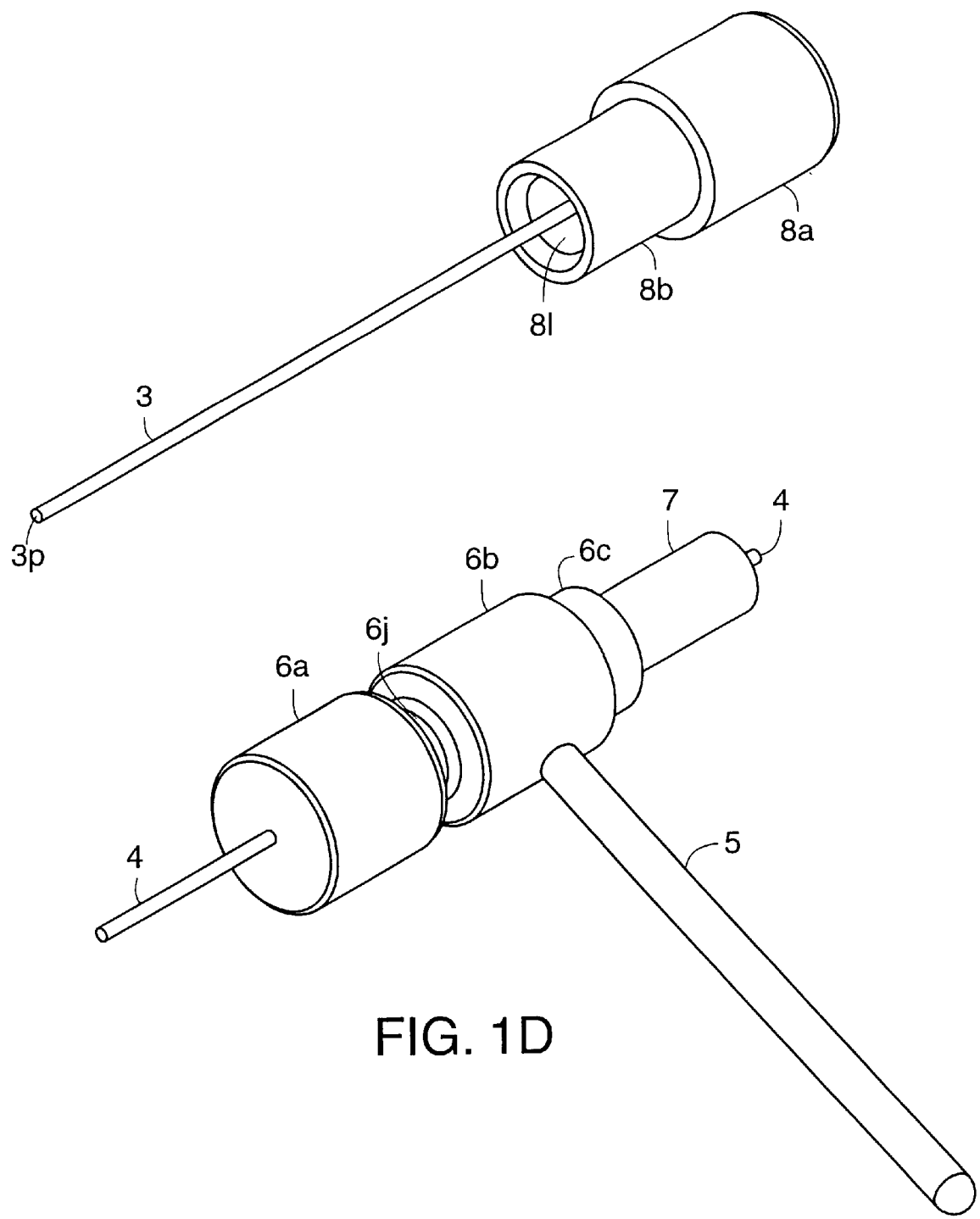
Figure 1E:
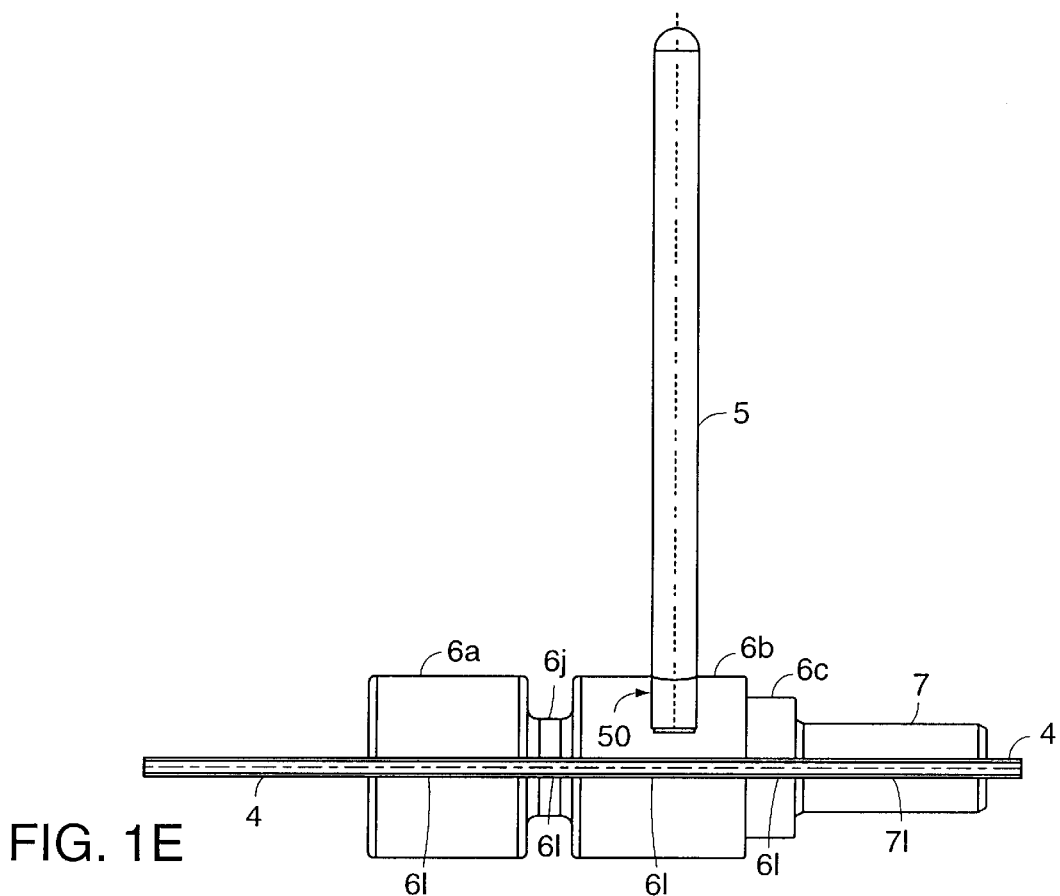
FIG. 1E and FIG. 1F show a cross-section through the longitudinal axis of components of the stylet.
Figure 1F:
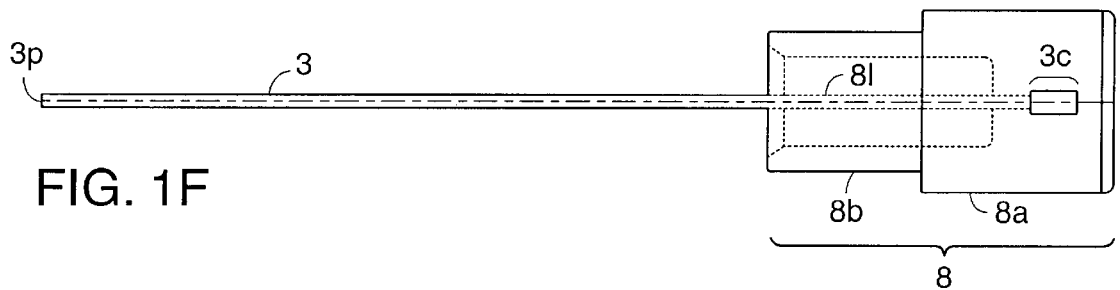
Figure 2A:
FIGS. 2A–2C show components of a stylet according to one embodiment of the invention.

As shown in FIG. 1A, in one embodiment according to the invention, the stylet 1 comprises a stylet body 2 and a stylet needle 3. The stylet needle 3, which is shown in cross-section in FIG. 2A, comprises a pushing surface 3p and a connecting end 3c (shown in FIG. 1e) for connecting the stylet needle 3 to the stylet body 2. The pushing surface 3p pushes either embedding media or tissue sample out of the coring needle. The stylet needle 3 preferably has any of the following properties: impact resistance, moisture resistance, abrasion resistance, chemical resistance (e.g., solvent resistance), static resistance, corrosion resistance; shatter resistance, static resistance, ability to maintain temperatures from −80° C. to 4° C., and combinations thereof.

In one embodiment according to the invention, the stylet needle 3 comprises stainless steel; however, other suitable materials include, but are not limited to: acetal (e.g., Delrin®, Celcon®, Ensital®); acrylic (e.g., Acrylite®, Plexiglas®, Lucite®, Staticon®); Acrylic-PVC Alloys; Acrylonitrile-Butadiene-Styrene (Cycolac®); FLUOROPLASTICS-Teflon (Teflon,® Kel-F,® Kynar,® Rulon,® Tefzel®); POILYCARBONATE (Lexan®, Hyzod®, Cyrolon®, Staticon®); POLYETHERETHERKETONE PEEK (VicTrex®); POLYETHERIMIDE (Ultem®); POLYOLEFINS Polyethylenes & Polypropylene (UHMW®) & Polyslick® 502; POLYURETHANE (Versathane®, Isoplast®); POLYVINYL CHLORIDE (PVC). The stylet needle 3 portion of the stylet 1 can be obtained from commercial sources, such as Precision Punch & Plastics (6102 Blue Circle Drive Minnetonka, Minn. 55343; www.precisionpunch.com). In one embodiment, at least the pushing surface 3p, comprises a non-stick surface, such as polypropylene, teflon, nylon, polyethylene, including derivatives or combinations thereof.

The dimensions of the stylet needle 3 can generally vary and are selected such that the diameter of the stylet needle 3 is slightly smaller than the diameter of the coring needle with which it will be used. In one embodiment the stylet needle 3 is cylindrical; however, the stylet needle 3 may be other shapes which conform to different shaped lumens of coring needles (e.g., rectangular, oval, polygonal and like). In one embodiment the sytlet needle 3 comprises a uniform cross-section; however, in another embodiment the pushing surface 3p of the stylet needle 3 conforms to the shape of the coring lumen of the coring needle for a slidable fit within the coring lumen but comprises a varying and smaller diameter cross-section for the remainder of its length.

Figure 2B:

In a preferred embodiment, the stylet needle 3 is protected from breakage by being supported and is at least partially enclosed within a stylet tube 4 (shown in FIG. 2B) for fitting the stylet needle 3 within the stylet body 2 and preventing rotation of the needle 3 within the tube 4. In one embodiment of the invention, the stylet tube 4 comprises stainless steel, such as $316^{th}$ stainless 21 and 23 gauge stainless steel. The support function of the stylet tube 4 is especially desirable when frozen tissues are being arrayed, given a generally higher pushing force needed to push frozen embedding matrix and/or frozen tissue out of the coring needle of the arrayer which causes the needles of the prior art to break frequently which necessitates stopping the arraying process to replace the stylet.

Figure 2C:
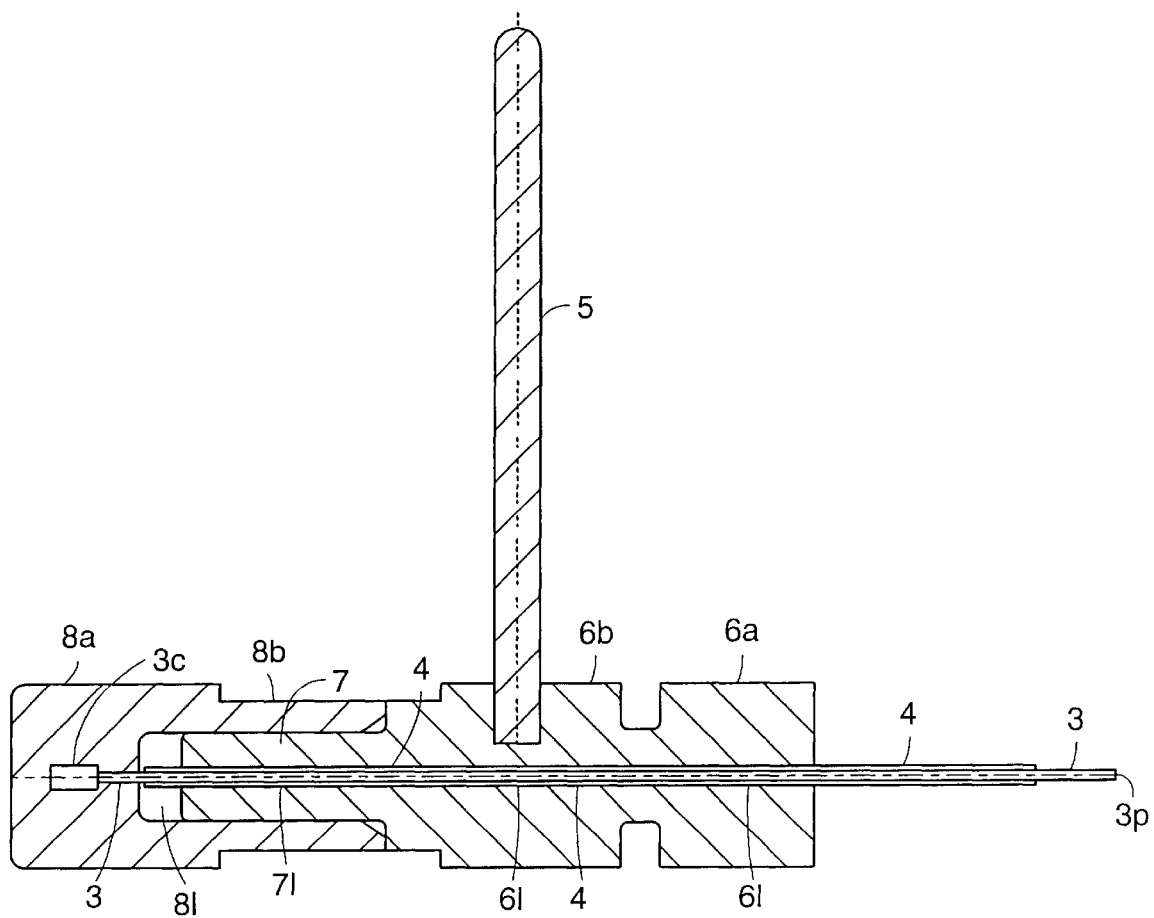

The stylet body 2 reinforces this support function. FIG. 2C shows the placement of the stylet needle 3 within the stylet body 2. In one embodiment of the invention, the stylet body 2 comprises polypropylene suitable plastic that will withstand low temperature impact forces. For example, suitable plastics include vinyls, thermoplastic elastomers, urethanes, or low-density olefins; polyolefins, polyesters, acrylics, polyamides, polyamid-imides, polyarylaulfones, polycarbonates, polyetherimides, polyethersulfones, polyetheretherketones, polyoxymethylyenes, polytetrafluoroethylenes, polystyrenes, polyurethanes; oriented or nonoriented polyethylene terephthalate, polypropylene, and blends, thereof. In a one embodiment, the stylet body 2 comprises mineral reinforced polypropylene which enhances the stiffness of the stylet body 2, such as RTP 136 mineral reinforced polypropylene from Imagineering Plastics®. In another embodiment of the invention the stylet body 2 comprises brass, such as 424 naval brass.

In addition to providing a support function, the stylet body 2 further provides a surface for connection with a stylet driver or other actuation means for moving the stylet 1. The actuation means can be electric, mechanical, or manual. When the actuation means is electrical, the stylet 1 preferably comprises at least a portion of an electrically conductive material, to allow the user to monitor and control movement of the stylet 1.

While the stylet body 2 can comprise a variety of shapes, in one embodiment, the stylet body 2 comprises a segmented base 6 and a connecting portion 7. The segmented base 6, in one embodiment, comprises at least a first segment 6a, a second segment 6b, and a third segment 6c.

Figure 3C:
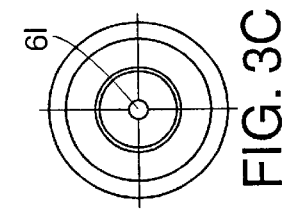
FIGS. 3A–F show different views of a stylet body according to one embodiment of the invention, comprising a segmented base and a stylet tube for receiving a stylet needle.
Figure 3B:
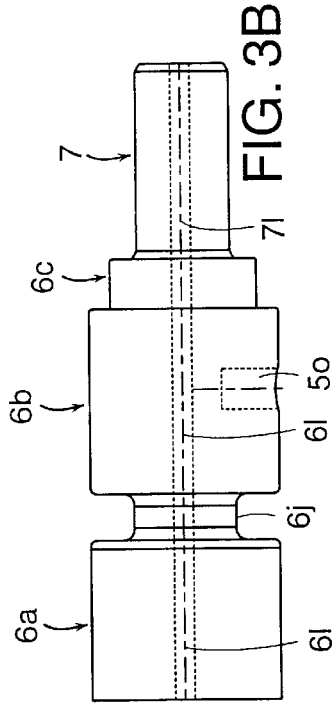
Figure 3E:
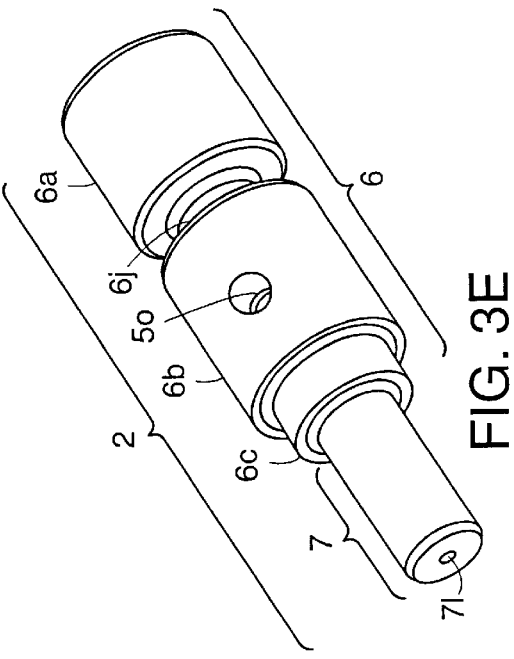
Figure 3F:
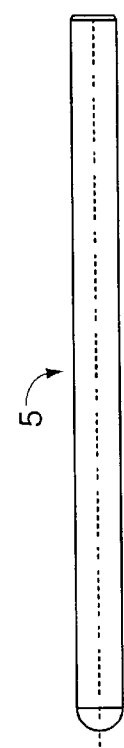
Figure 3D:
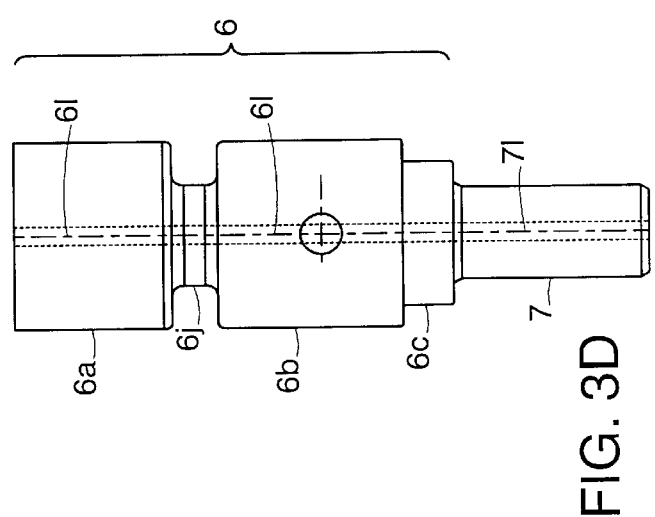
Figure 3A:
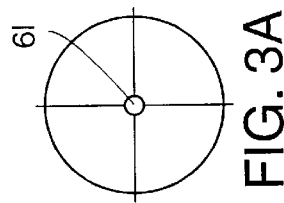

In one embodiment, at least the connecting portion 7 comprises a lumen 71 (shown in cross-section in FIG. 3A) for fitting the stylet tube 4 and/or stylet needle 3. However, in the embodiment shown in FIGS. 3C–3E, the segmented base 6 of the stylet body 2 also comprises a lumen 61 (shown in cross-section in FIG. 3C). In still a further embodiment of the invention, at least two of the segments (6a, 6b, 6c) of the stylet body are connected by joining segment 6j which can be a smaller diameter than the outer diameter of the segments 6a, 6b, 6c (see FIGS. 3B–3E). In one embodiment, the joining section 6j provides a surface for coupling with the automatic tissue microarrayer, e.g., a surface for fitting onto a dowel in tissue arrayer which holds the stylet in a fixed horizontal position, relative to the surface of the recipient or donor block.

In one embodiment, one of the segments (any of 6a, 6b, or 6c) comprises an opening 5o for inserting a grasping element or handle 5. The handle 5 provides the user with the capability of grasping and manipulating the stylet 1 without contacting any surfaces (e.g., 3p) which contact tissue or embedding media. In one embodiment the handle 5 is removable from the stylet body 2; however, in another embodiment, the handle 5 is an integral part of the stylet body 6. The shape of the handle 5 can also vary. In one embodiment shown in FIG. 3F, the stylet handle 5 is cylindrical or dowel-shaped. Although stylet handle 5 materials can be generally varied; in one embodiment, the stylet handle 5 is stainless steel, such as 18.8 gauge stainless steel. The handle 5 facilitates manual removal of the stylet 1 from an automatic tissue arrayer.

In another embodiment of the invention, the stylet body 2 comprises a stylet cap 8 for connecting to the connecting portion 3c of the stylet needle 3 and further stabilizing and preventing axial movement of the needle within the sylet body 2. The stylet cap 8 like the stylet base 6, can be segmented. For example, as shown in FIG. 1C, the stylet cap 8 comprises a first cap segment 8a and second cap segment 8b. At least one segment comprises a lumen 81 for receiving the stylet needle 3.

In one embodiment of the invention, the stylet needle 3, which is capped at one end with the cap 8, fits into the stylet tube 4, bringing the stylet base 6 and connecting portion 7 into proximity with the stylet cap 8 (see FIG. 1A). Therefore, in this embodiment, the lumen 81 is also large enough to fit the connecting portion 7 of the stylet body. In a further embodiment of the invention, a resilient element 9 (e.g., a spring) is placed between stylet base 6 and the stylet cap 8. In the embodiment shown in FIG. 1A, the spring 9 abuts segment 8a of the stylet cap 8 and segment 6b of the stylet base. The spring translates linear force on the pushing surface 3p (e.g., from a stylet driver) of the stylet needle 3 into a reverse linear force on the stylet cap 8, driving the stylet backwards after it pushes tissue or embedding media out of the coring needle.

In a further embodiment of the invention, shown in FIG. 2C, when the stylet needle surface is in contact with tissue or embedding media, the connecting portion of the stylet body 2 is driven into the lumen 81 of the stylet cap 8 and reactive linear force is stored in the spring 9 (shown in FIG. 2C) until pressure on the stylet needle pushing surface 3p is released. When pressure is released, the linear force acts on the portion of the stylet cap 8 in contact with the spring 9, pushing it backwards.

Figure 5A:
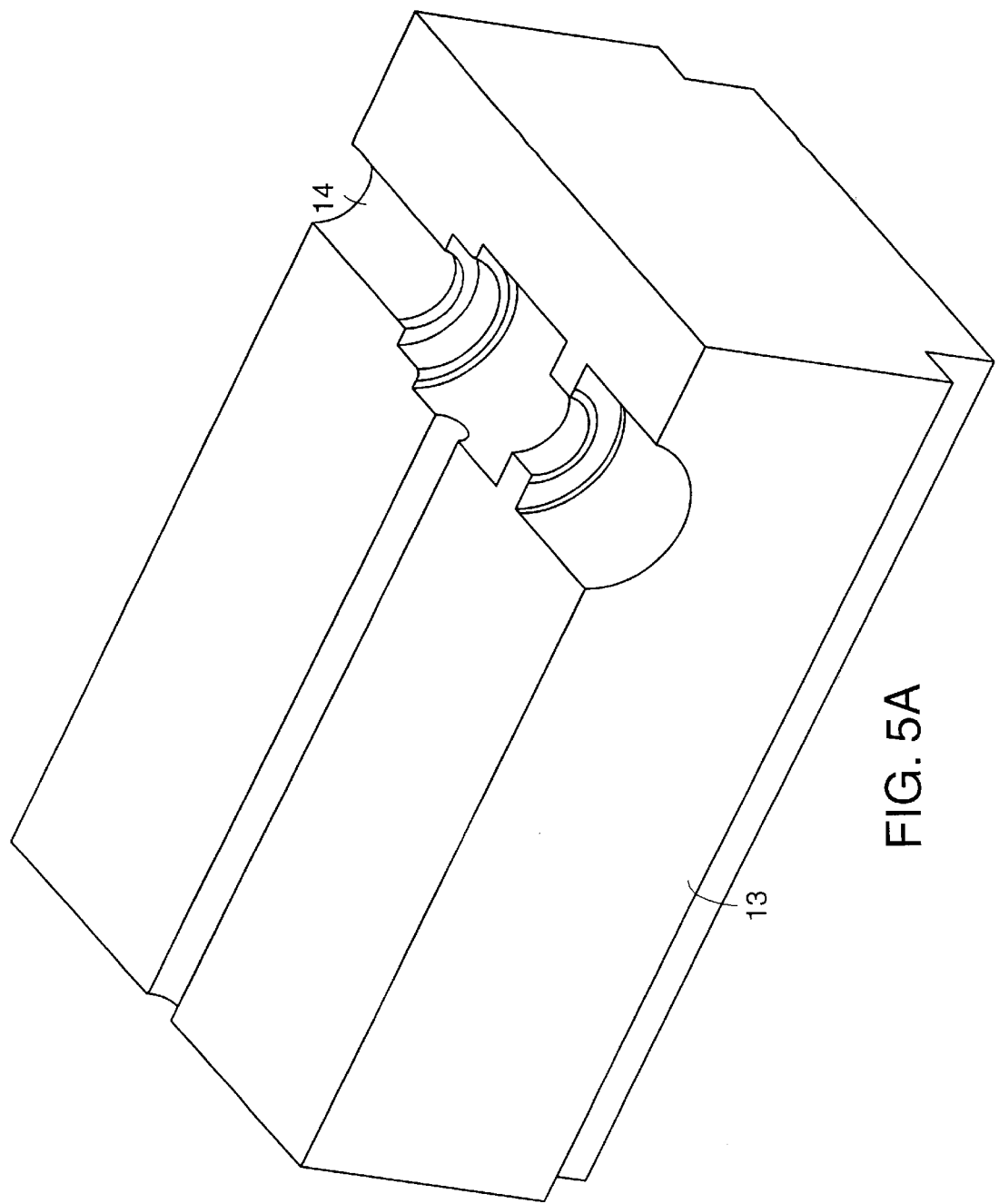
FIGS. 5A–5D show different views of mold half which comprises a half mold cavity, with exemplary dimensions. The mold cavity corresponds in shape to the segmented base and connecting portion of the stylet body.
Figure 4A:
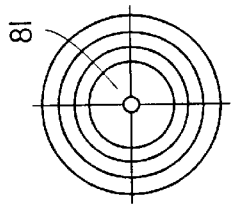
FIGS. 4A and 4B show a stylet cap according to one embodiment of the invention.
Figure 4B:
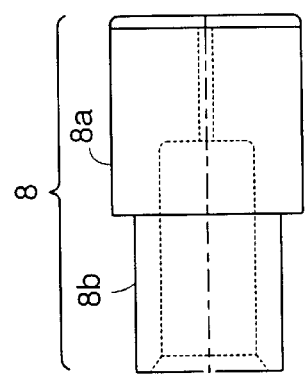
Figure 5B:
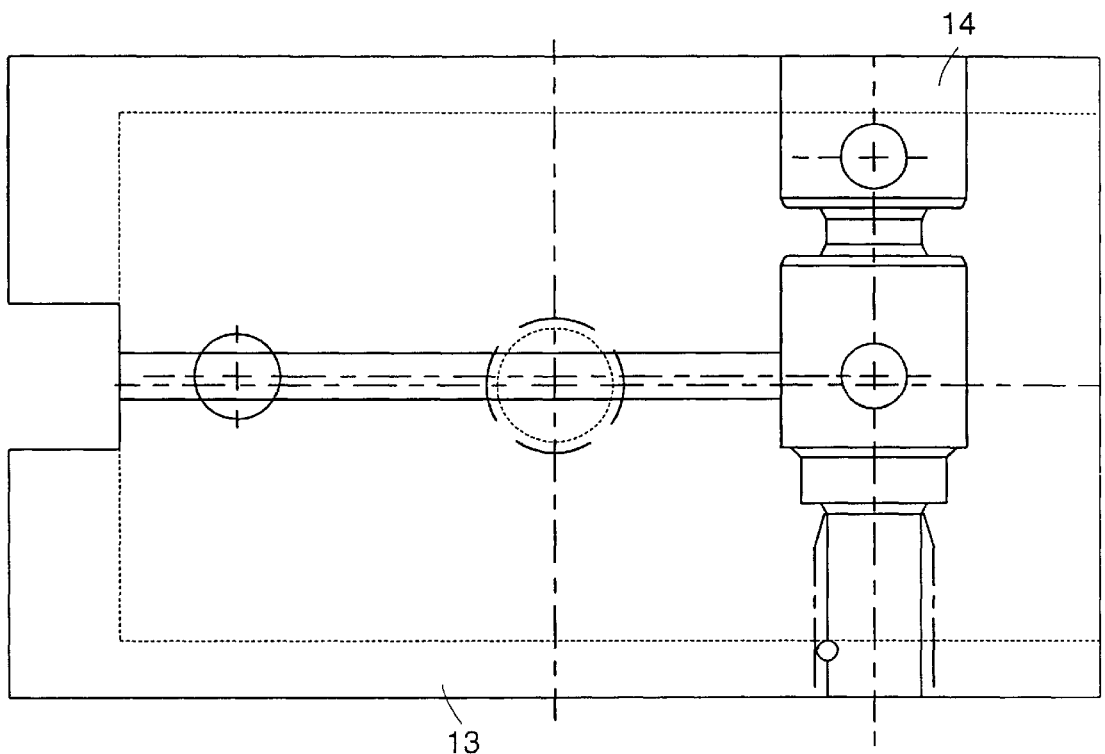
Figure 5C:
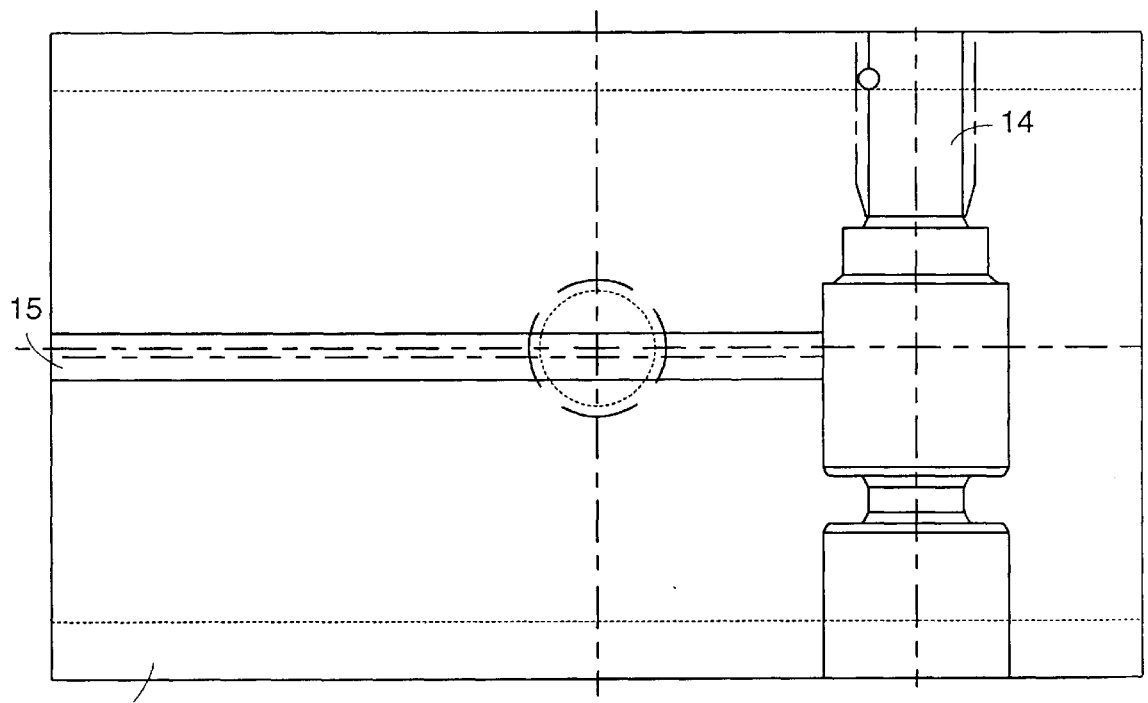

The stylet body 2 and stylet needle 3, in one embodiment, are formed separately by injection molding of component pieces. Suitable molds for forming the components of the stylet 1 are shown in FIGS. 5A–D. In one embodiment, the mold comprises two identical halves, each of which comprises a half mold cavity 14 corresponding in shape to the external surface of half of a particular component of the stylet. For example, FIGS. 5A–5C show different views of mold half 13 which comprises a half mold cavity 14. In this embodiment, the half mold cavity 14 corresponds in shape to the segmented base 6 and connecting portion 7 of the stylet body 2.

Figure 5D:
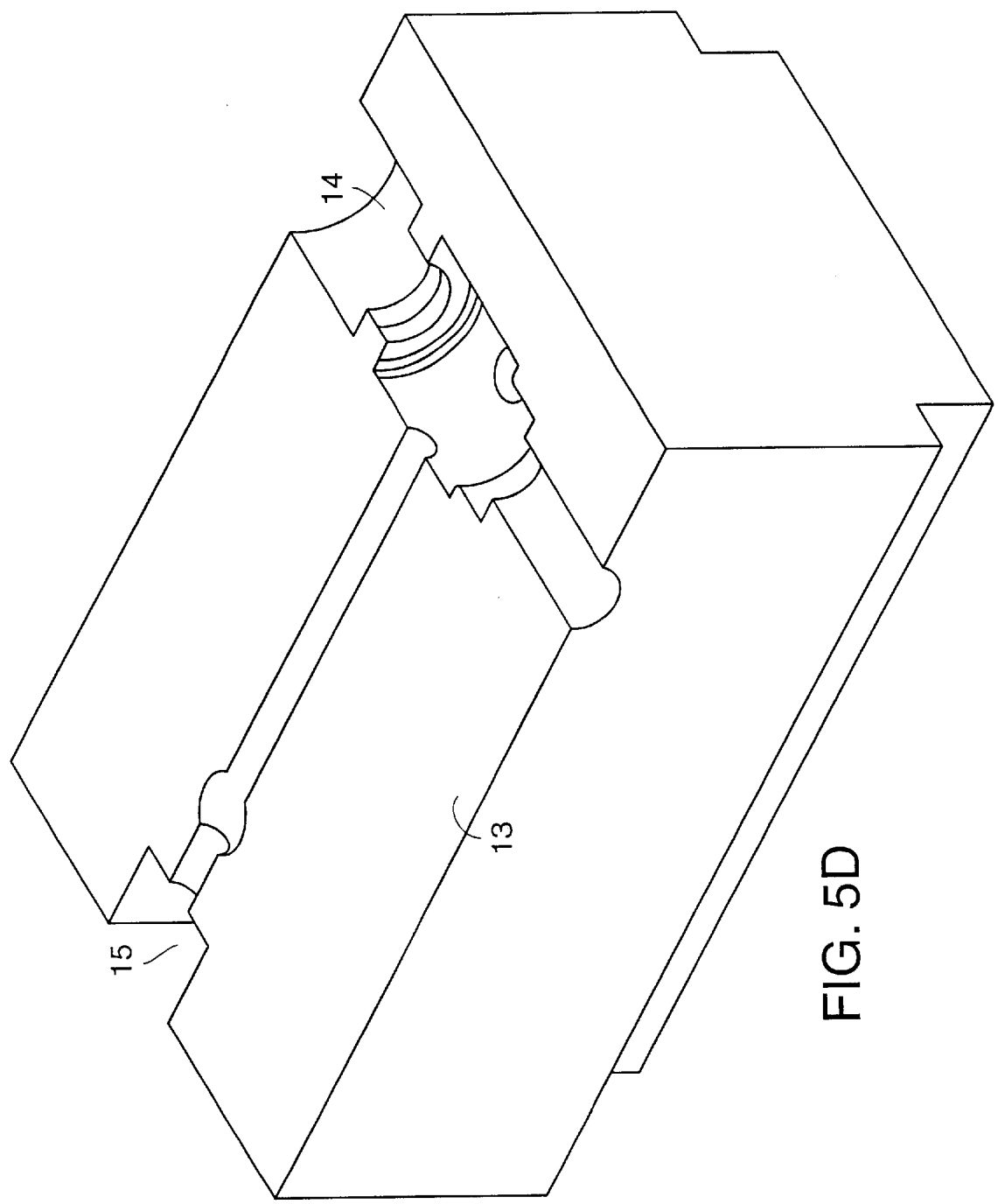
Figure 7A:
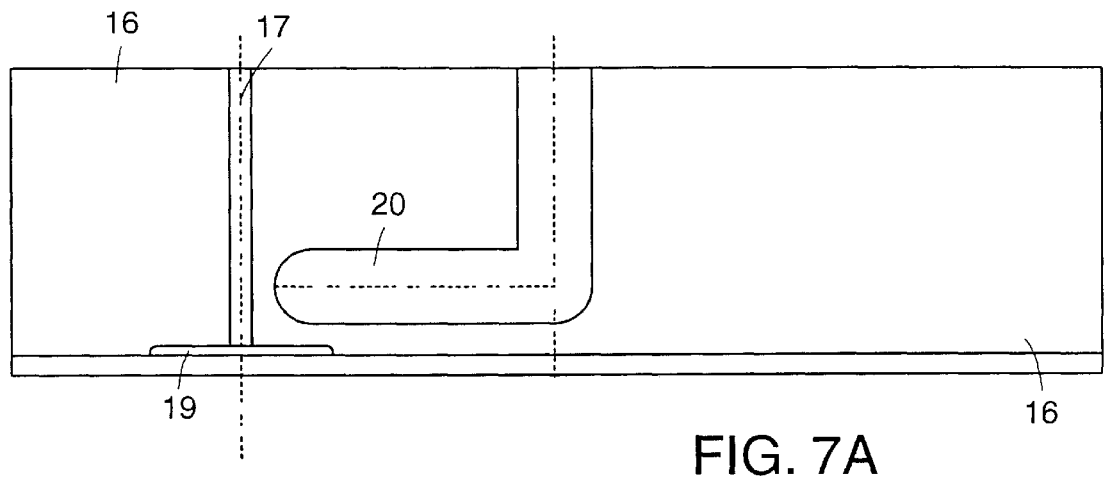
FIGS. 7A–H show different views of a mold half for forming a stylet tube 4.
Figure 7B:
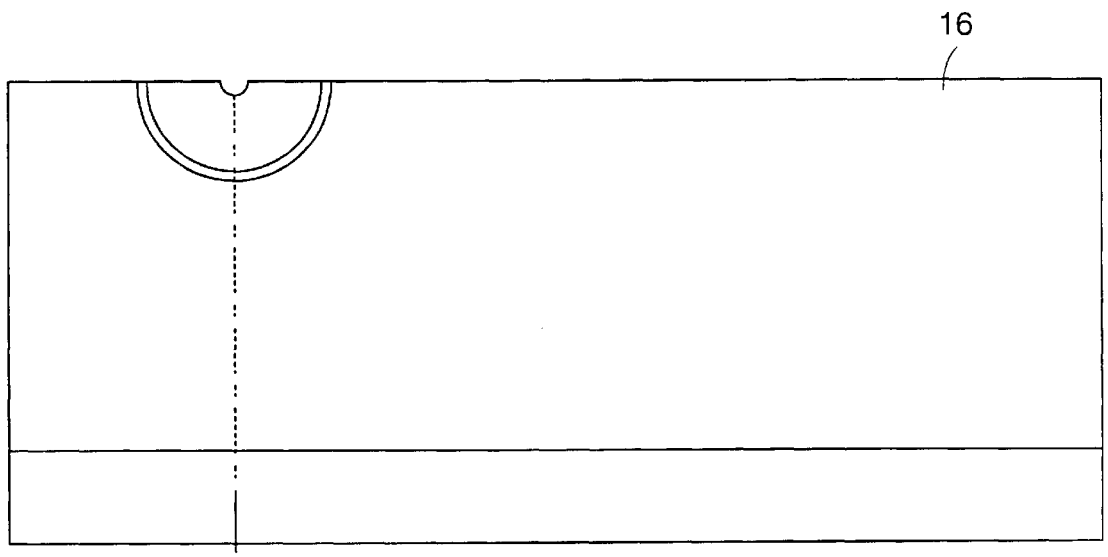
Figure 7C:
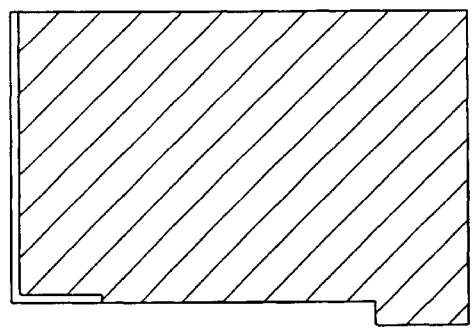
Figure 7D:
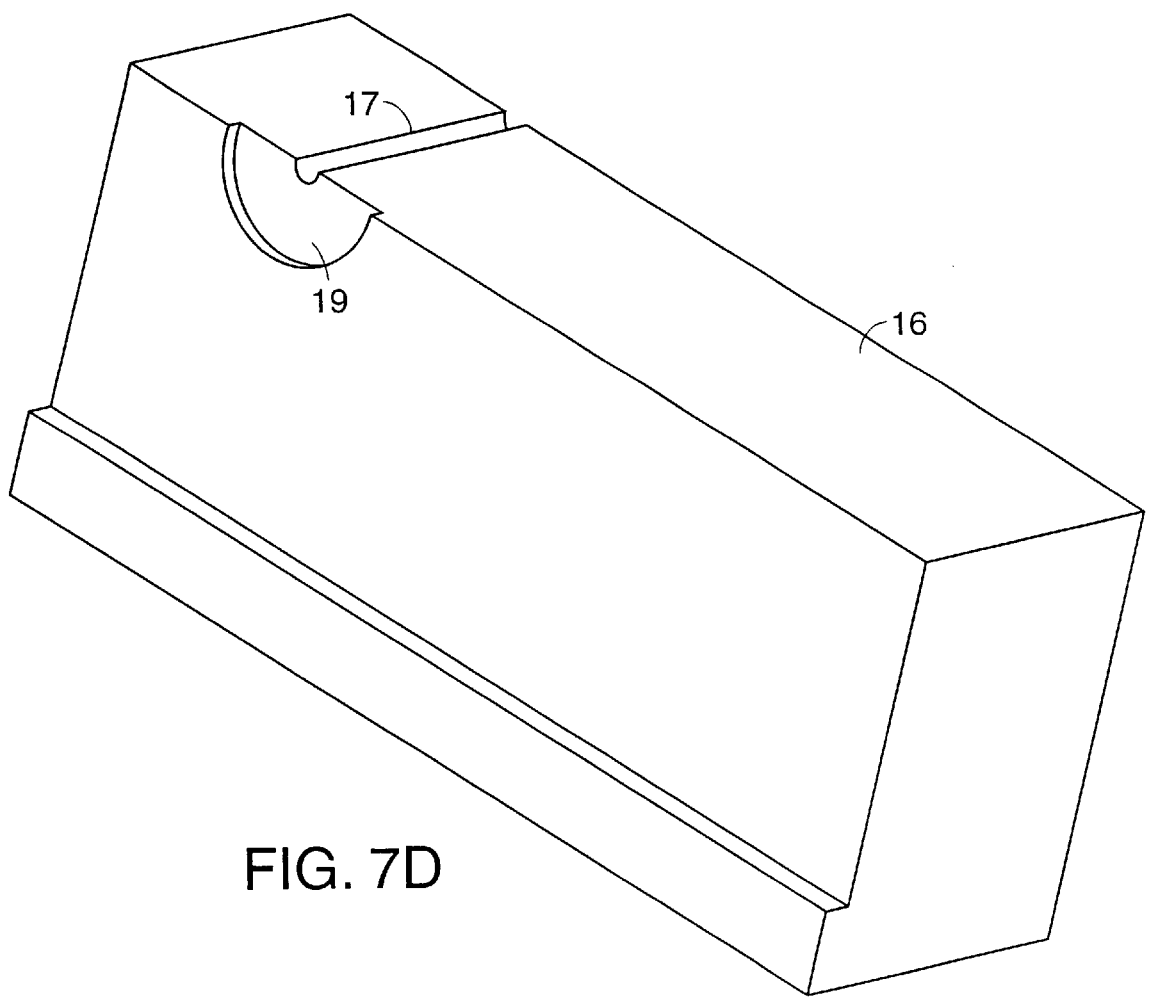
Figure 7E:
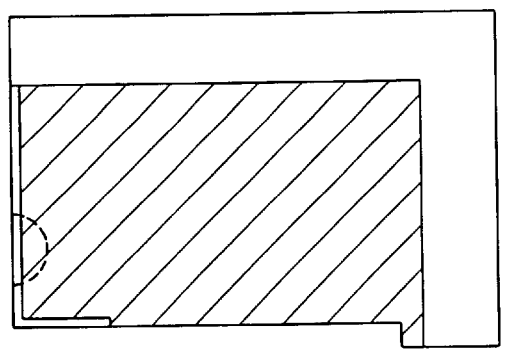
Figure 7F:
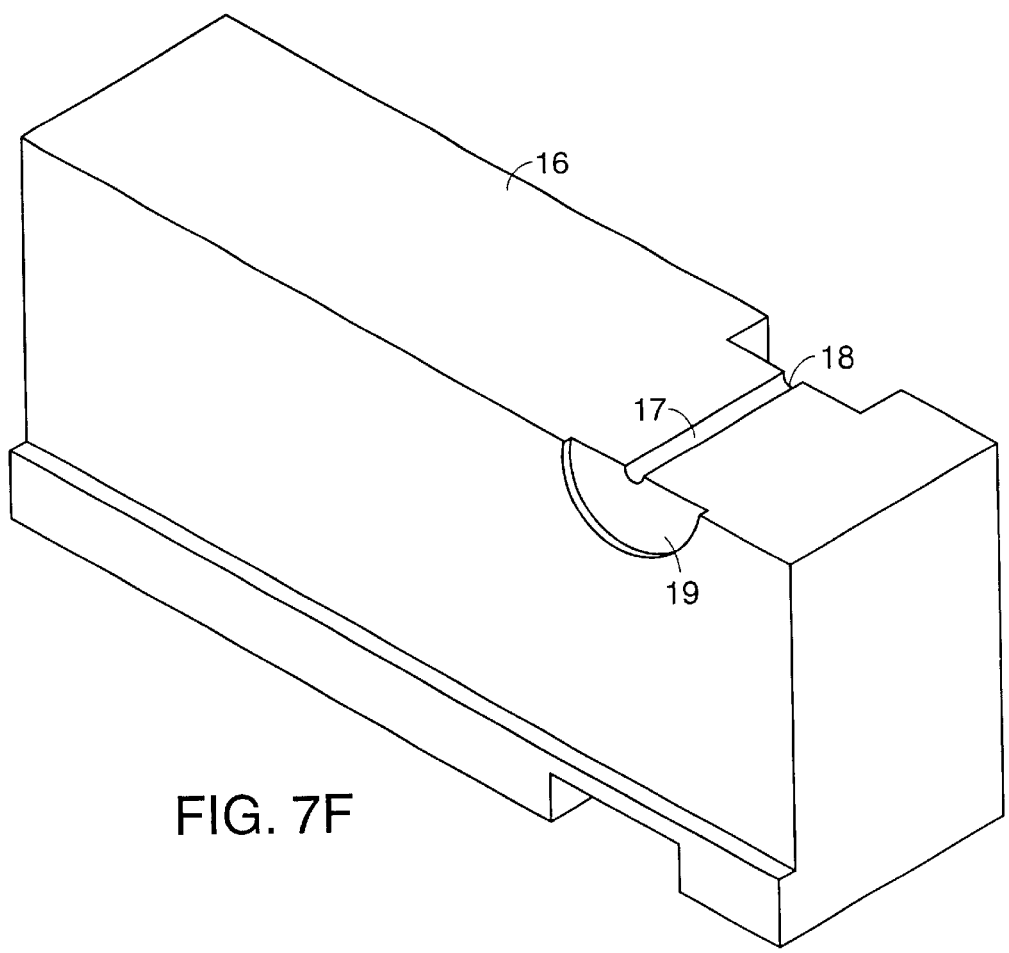
Figure 7G:
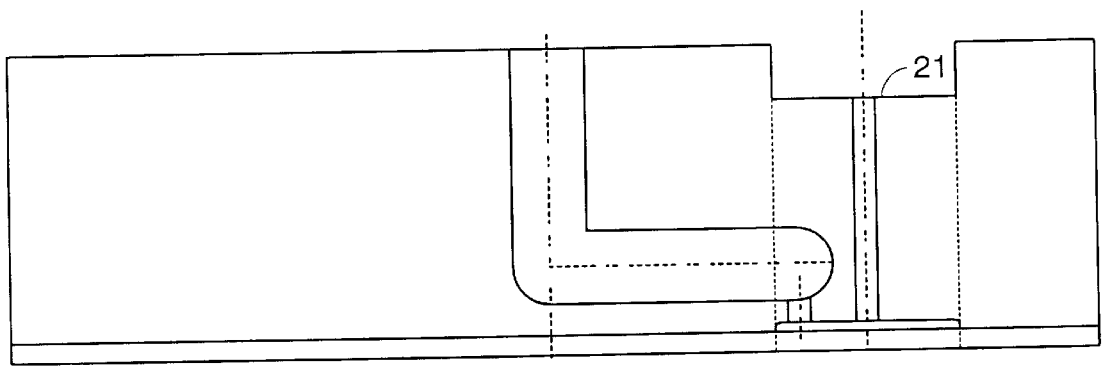
Figure 7H:
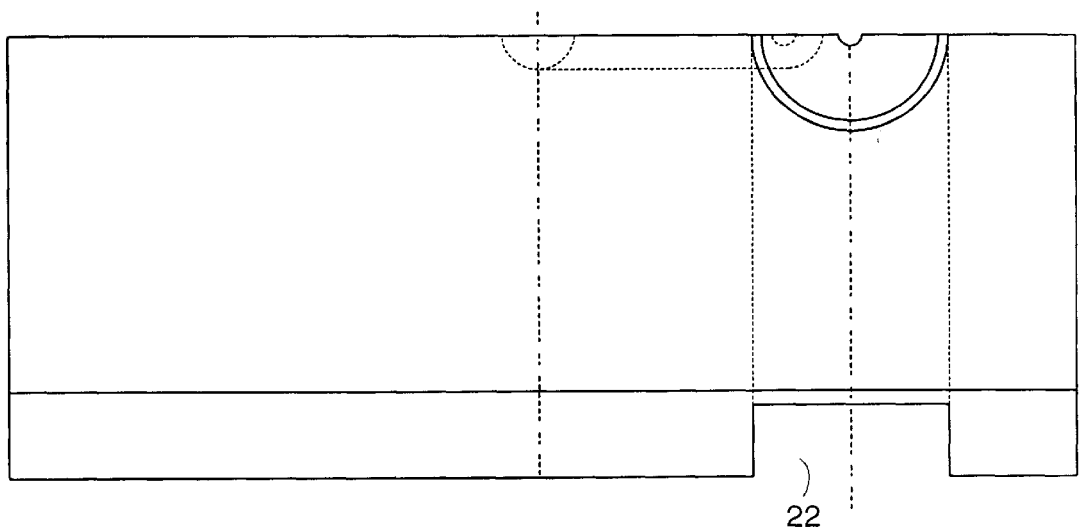
Figure 8A:
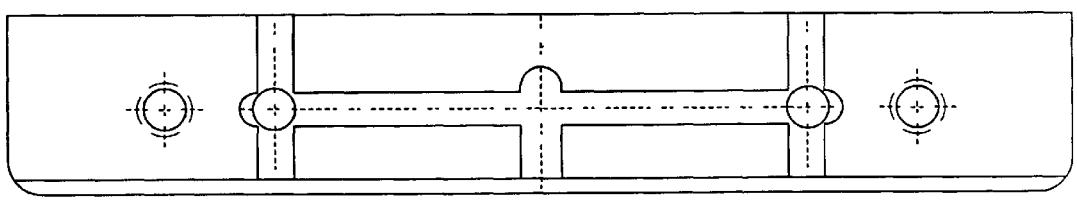
FIGS. 8A–D show different views of a mold half which forms a runner block.
Figure 8B:
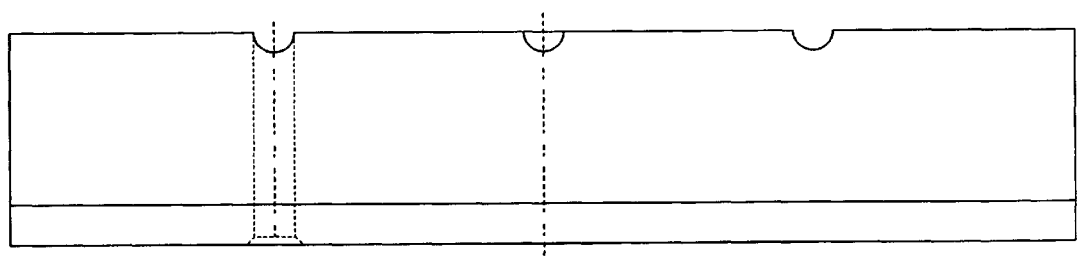
Figure 8C:
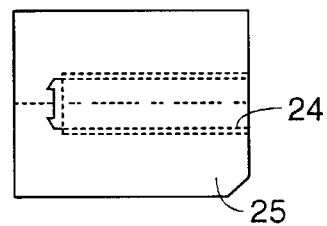
Figure 8D:
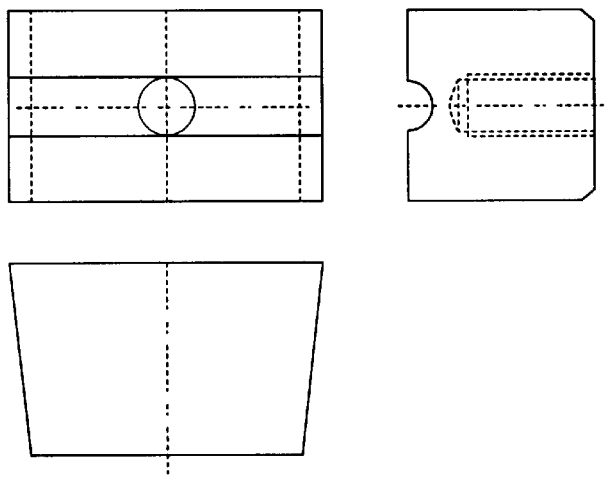
Figure 9:
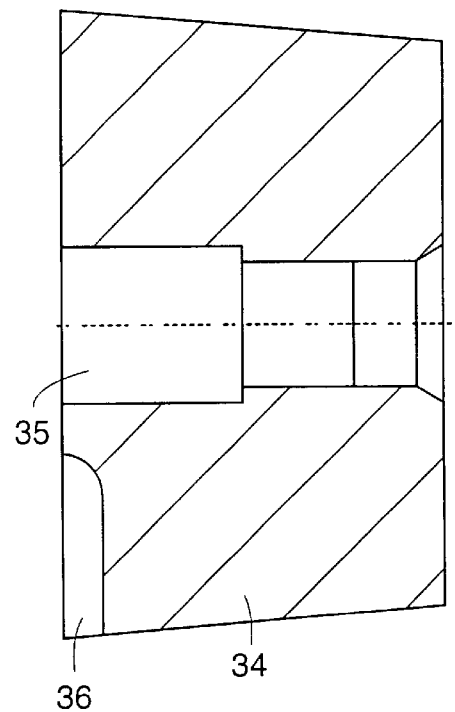
FIGS. 9 shows different views of a mold half for forming a stripper for ejectng a core pin from a mold, with exemplary dimensions.

When forming the stylet body, two mold halves 13 are held together and aligned by connecting elements (e.g., by connecting pins, screws, or bolts, not shown), and the material which forms the stylet body is injected into the mold cavity through an opening 15 in the mold that communicates with the mold cavity (shown in FIGS. 5C–5D). In this embodiment, the opening 15 may be provided in one or both mold halves. The temperature of the mold 13 itself is kept at temperature which is lower than the melting point of the plastic being injected into the mold cavity, as a means of lowering the temperature of the plastic as it flows into the mold cavity. The injected mold is allowed to cool and after cooling, the connecting elements are removed and the two mold halves separated. The mold can be cleaned using alcohol, heptane, or some other type of solvent applied to a lint free applicator. In one embodiment, after cleaning the mold can be dried using compressed air.

FIGS. 6A–C, show different views of a mold for forming the stylet cap 8 according to one embodiment of the invention and suitable dimensions of the mold. While FIGS. 7A–F show different views of a mold half 16 for forming a stylet tube 4. The mold half 16 comprises a mold cavity 17 corresponding in shape to the stylet tube 4 and comprising an opening 17 for injecting stylet tune-forming materials. In the embodiment shown in FIGS. 7D and 7F, the mold further comprises a cavity for forming a portion of the stylet body 79. This embodiment serves to stabilizes the stylet tube 4, by preventing it from movement within the stylet body 6.

In one embodiment, a mold core (not shown) is provided which is used to define the internal surface of the stylet 1. For example, in one embodiment, a core is provided for defining a lumen 81 within the stylet cap 8. In this embodiment, the core is placed within the mold cavity formed by two mold halves 14, and injected polymer flows around the core to form the remainder of the stylet cap 8. The core is then removed after the polymer cools, creating a lumen in the space which had been previously occupied by the core. In one embodiment, the core is kept in place inside the mold cavity by pins which couple the core to the mold body 13, until the polymer is cooled. The core may be ejected from the mold through the use of a stripper (see, e.g., such as the one shown in FIGS. 10A–C). The core itself may also be generated by injection molding.

In another embodiment, molds are provided for generating multiple stylet components at once, i.e., by providing multiple mold cavities within each mold. In one embodiment, each mold is capable of generating two components at a time. In another embodiment, each mold is capable of generating four components at a time. In a further embodiment of the invention, multiple stylet components are generated using a single injection molding device (for example a multi-valved injection device) and polymer is diverted to the appropriate molds and cavities by at least one runner block which comprises a plurality of channels for directing streams of polymers to the appropriate mold cavities. FIGS. 8A–D show different views of a mold half which forms an exemplary runner block according to the invention.

It should be obvious to those of skill in the art that different, and/or additional molds can be used to generate stylets according to the invention, and that these are encompassed within the scope of the instant invention.

Although the stylets according to the invention are optimally designed for use with tissue microarrayers which array frozen tissues, they can also be used with tissue microarrayers for microarraying paraffin-embedded and plastic-embedded tissues. In one embodiment, the stylets according to the invention are used in microarraying mixed format microarrays, e.g., comprising both paraffin and frozen tissue sections (disclosed in U.S. Provisional Application Serial No. 60/236,649, filed Sep. 29, 2000, the entirety of which is incorporated herein by reference. In a further embodiment, the stylets according to the invention are used in arraying large format arrays disclosed in U.S. Provisional Application No. 60/234,493, filed Sep. 22, 2000, the entirety of which is incorporated by reference herein. In this embodiment, the diameter of the stylet needle's pushing surface is greater than 0.6 mm, and preferably ranges from 0.7 mm to 5 mm.

Unlike stylets, the stylets according to the instant invention are inexpensive to make, disposable, and can be reused multiple times in an automatic tissue microarrayer. The stylets are particularly ideal for use in arraying frozen tissues because the unique design of the stylet is resistant to breakage.

Variations, modifications, and other implementations of what is described herein will occur to those of ordinary skill in the art without departing from the spirit and scope of the invention.

What is claimed is:

1. A stylet for removing tissue or embedding media from a coring needle, comprising:

a stylet needle comprising a pushing surface and a connecting end, said pushing surface for pushing tissue or embedding media from said coring needle, said connecting end for connecting to a stylet body;

a stylet support tube extending from the stylet body that surrounds a portion of the stylet needle;

a stylet body comprising a lumen for receiving at least said connecting end of said stylet needle and for preventing rotation of said stylet needle within said stylet body; and wherein at least said pushing surface of said stylet needle comprises a material which can maintain a temperature from −20° to 4° C. during the process of removing tissue or embedding material from said coring needle.

2. The stylet according to claim 1, wherein the diameter of said stylet needle's pushing surface is greater than 0.6 mm.

3. The stylet according to claim 2, wherein said diameter ranges from 0.7 mm to 5 mm.

4. The stylet according to claim 1, wherein the diameter of the pushing surface is less than 0.6 mm in diameter.

5. The stylet according to claim 1, wherein the diameter of the pushing surface is at least 2 mm.

6. The stylet according to claim 1, for slideably fitting within a coring needle ranging from 0.3 to 2.0 mm in diameter.

7. The stylet according to claim 1, wherein said stylet needle comprises steel or plastic.

8. The method according to claim 1, wherein said pushing surface of the stylet needle is a non-stick surface.

9. The stylet according to claim 8, wherein said non-stick surface is selected from the group consisting of: polypropylene, teflon, nylon, polyethylene, derivatives and combinations thereof.

10. The stylet according to claim 1, wherein said stylet body comprises polypropylene or brass.

11. The stylet according to claim 1, wherein said stylet body comprises a stylet base and a stylet cap, said stylet cap for receiving at least the connecting end of said stylet, said stylet base for slideably moving along the length of the stylet needle distal to the connecting end.

12. The stylet according to claim 11, wherein said stylet cap and stylet base are separated by a resilient element.

13. The stylet, according to claim 12, wherein said resilient element is a spring.

14. The stylet according to claim 1, wherein said stylet support tube prevents rotation of the needle within said stylet support tube.

15. The stylet according to claim 1, wherein said stylet body comprises an opening for receiving a graspable element.

16. The stylet, according to claim 15, wherein said stylet comprises said graspable element inserted partially within said opening.

17. The stylet according to claim 1, wherein said stylet body comprises a plastic that withstands low temperature impact forces.

18. The stylet according to claim 1, wherein said stylet body comprises mineral reinforced polypropylene.

19. The stylet according to claim 1, further comprising a surface for connection with an actuation means for moving the stylet.

20. The stylet according to claim 1, further comprising a joining section for coupling to a tissue microarrayer.

21. The stylet according to claim 20, wherein said joining section comprises a surface for fitting onto a dowel in a tissue microarrayer, said dowel holding said stylet is a fixed position.

\* \* \* \* \*